United States Patent
Kowalik et al.

(10) Patent No.: US 12,349,986 B2
(45) Date of Patent: Jul. 8, 2025

(54) DEVICE AND METHOD FOR 3D REAL-TIME MEDICAL INSTRUMENT TRACKING

(71) Applicants: Siemens Healthineers AG, Forchheim (DE); King's College London, London (GB)

(72) Inventors: Grzegorz Kowalik, London (GB); Radhouene Neji, London (GB); Reza Razavi, Northwood (GB); Kuberan Pushparajah, London (GB); Sebastien Roujol, Kingston upon Thames (GB)

(73) Assignees: Siemens Healthineers AG, Forchheim (DE); King's College London, London (GB)

( * ) Notice: Subject to any disclaimer, the term of this patent is extended or adjusted under 35 U.S.C. 154(b) by 3 days.

(21) Appl. No.: 18/401,883

(22) Filed: Jan. 2, 2024

(65) Prior Publication Data

US 2025/0017665 A1 Jan. 16, 2025

(30) Foreign Application Priority Data

Jan. 24, 2023 (EP) .................................... 23153006

(51) Int. Cl.
*A61B 34/20* (2016.01)
*A61B 5/055* (2006.01)
*G01R 33/56* (2006.01)

(52) U.S. Cl.
CPC ............. *A61B 34/20* (2016.02); *A61B 5/055* (2013.01); *G01R 33/5607* (2013.01); *A61B 2034/2051* (2016.02); *A61B 2034/2065* (2016.02)

(58) Field of Classification Search
CPC . A61B 34/20; A61B 5/055; A61B 2034/2051; A61B 2034/2065;
(Continued)

(56) References Cited

U.S. PATENT DOCUMENTS 6,006,126 A * 12/1999 Cosman ................. A61B 34/20
600/417
6,476,607 B1 * 11/2002 Dannels ............. G01R 33/4833
324/309

(Continued)

FOREIGN PATENT DOCUMENTS

WO 0246784 A2 6/2002

OTHER PUBLICATIONS

Vidya Shankar, Rohini, et al. "Real-time automatic image-based slice tracking of gadolinium-filled balloon wedge catheter during MR-guided cardiac catheterization: A proof-of-concept study." Magnetic resonance in medicine 91.1 (2024): 388-397. (10 pages).

*Primary Examiner* — Sanjay Cattungal
(74) *Attorney, Agent, or Firm* — Lempia Summerfield Katz LLC (57) ABSTRACT

A method and a magnetic resonance tomography unit for tracking a medical instrument are disclosed. In the method, a tracking volume is defined enclosing a predefined trajectory of the medical instrument. Two-dimensional (2D) projection images of the tracking volume in presence of the medical instrument are acquired with the magnetic resonance tomography unit from two different view angles. Reference 2D images for the two view angles are determined and a background of the 2D projection images is suppressed. Two sets of 2D coordinates of the medical instrument are extracted from the two 2D projection images and combined to a 3D coordinate set and output on a display.

15 Claims, 4 Drawing Sheets

(58) Field of Classification Search
CPC ............ A61B 34/25; A61B 2034/2046; G01R 33/5607; G01R 33/285; G01R 33/5608
See application file for complete search history.

(56) References Cited

U.S. PATENT DOCUMENTS

| | | | | |
|---|---|---|---|---|
| 2007/0043288 | A1* | 2/2007 | Mueller | G01R 33/287 |
| | | | | 600/411 |
| 2007/0249934 | A1* | 10/2007 | Aksit | G01R 33/34084 |
| | | | | 600/427 |
| 2012/0089008 | A1* | 4/2012 | Strehl | G01R 33/286 |
| | | | | 600/411 |
| 2013/0033700 | A1* | 2/2013 | Hallil | A61N 5/1071 |
| | | | | 378/63 |
| 2013/0060146 | A1* | 3/2013 | Yang | A61B 34/20 |
| | | | | 600/476 |
| 2016/0066794 | A1* | 3/2016 | Klinder | A61B 5/02028 |
| | | | | 600/424 |
| 2016/0102969 | A1* | 4/2016 | Verstege | A61B 1/009 |
| | | | | 250/206 |
| 2018/0008351 | A1* | 1/2018 | Schoenefeld | A61B 17/15 |
| 2018/0021097 | A1* | 1/2018 | Quaid | A61B 34/10 |
| | | | | 600/407 |

* cited by examiner

DEVICE AND METHOD FOR 3D REAL-TIME MEDICAL INSTRUMENT TRACKING

The present patent document claims the benefit of European Patent Application No. 23153006.4, filed Jan. 24, 2023, which is hereby incorporated by reference in its entirety.

TECHNICAL FIELD

The disclosure is related to a method and a magnetic resonance tomography unit for tracking a medical instrument. A tracking volume is defined enclosing a predefined trajectory of the medical instrument. Images of the tracking volume in presence of the medical instrument are acquired with the magnetic resonance tomography unit and coordinates of the medical instrument are extracted and output on a display.

BACKGROUND

Magnetic computer tomographs are imaging facilities, which, for imaging an examination object, align nuclear spins of the examination object with a strong external magnetic field and excite them with a magnetic alternating field for precession about this alignment. The precession or return of the spins from this excited state back into a state with lower energy in its turn creates as a response a magnetic alternating field, which is received via antennas.

A spatial encoding is impressed on the signals with the aid of magnetic gradient fields, which subsequently makes it possible to assign the received signal to a volume element. The received signal is then evaluated and a three-dimensional (3D) image representation of the examination object is provided.

Such full 3D image acquisition requires some time to reach a sufficient image quality, in particular signal to noise ratio. Furthermore, most medical instruments made from metal or plastics cannot be imaged directly by the magnetic resonance tomography, as the material of the instrument does either provide no magneto-resonance active spins or at least not at a frequency like the Larmor frequency may be used for imaging the water in the body of a patient. Unless the medial instruments are provided with magnet-resonance active materials or devices, which add to the dimensions of the device or are costly, the imaging of the medical instrument relies on indirect effects like absence of water in the device or artefacts generated by the conductivity or different susceptibility of the material of the medical device, which makes imaging even more difficult. When real time tracking of a device is required, the short integration times do not allow full 3D imaging at a sufficient image quality.

SUMMARY AND DESCRIPTION

It is therefore an object of the disclosure to improve the tracking of a medical instrument.

The object is achieved by a method for operation of a magnetic resonance tomograph and by a magnetic resonance tomograph as described herein. The scope of the present disclosure is defined solely by the appended claims and is not affected to any degree by the statements within this summary. The present embodiments may obviate one or more of the drawbacks or limitations in the related art.

The method as described herein is a method for tracking a medical instrument with a magnetic resonance tomograph in real time. "Real time" in this context means that the image repetition rate is high enough such that an operator may track and control the movement of the medical instrument, e.g., with an image repetition rate higher than 1 f/s (frames per second), 5 f/s, or 10 f/s.

The method is executed by a magnetic resonance tomograph that includes a control unit for controlling all subsystems like gradient generation and radio frequency (RF) transmission and reception for image acquisition and also for the image reconstruction, analysis, and display. The control unit may also be separated in different sub-systems for each task.

In one act of the method, a tracking volume is defined or determined by the control unit. A tracking volume is defined as a volume in the field of view of the magnetic resonance tomograph which encloses a predefined trajectory of the medical instrument. The predefined trajectory may be entered by an operator or transferred as data from a treatment planning system. The trajectory describes a path along which the medical instrument shall be moved. The tracking volume may be determined by a cuboid wherein the surfaces are determined by six planes orthogonal to the axes of a coordinate system in which the trajectory is defined. The coordinates where the planes intersect with the axes are the minimum and the maximum value of the coordinate of the trajectory along each axe. Other non-orthogonal coordinate systems and tracking volumes may also be considered, wherein the trajectory is included by the tracking volume. The tracking volume may also be changed during execution of the method, which might be considered as starting with a new instance of the method.

In another act of the method, a first two-dimensional (2D) projection image of the tracking volume is acquired by the control unit in presence of the medical instrument with the magnetic resonance tomography unit. The tracking volume is, as explained before, a three-dimensional volume that extends in all three directions of space. In particular, for the object to be imaged with a resolution of r, (i.e., the volume elements to be image being cubes with a side length r), the tracking volume has an extension in each dimension of a multiple of r. A 2D projection image of the tracking volume is a 2D image, (i.e., an array of pixels arranged in a matrix in a 2D surface, e.g., a plane or a piece of a plane). The plane may be considered as a section plane through the tracking volume.

Each pixel is assigned a value. In a 2D projection image, this value is not assigned to the magnetic resonance signal of a single volume element or voxel in the tracking volume but derives from a plurality of voxels arranged along a line through the pixel in a projection direction. The projection direction may be perpendicular to the 2D surface. In certain examples, the values of each voxel along the line sum up to a value assigned to the pixel. This is similar to a 2D X-ray image, wherein the attenuation factors of all volume elements along the x-ray beam direction sum up to the pixel value in the x-ray image.

The contrast of the image acquisition of the first 2D projection image may be enhanced by contrast improving steps like partial saturation pre-pulses.

In a similar way, in another act, a second 2D projection image is acquired. A first projection direction or projection vector for the first 2D projection image is different from a second projection vector of the second 2D projection image. The first projection vector and the second projection vector enclose an angle larger than 30 degrees or 60 degrees, (e.g., equal to 90 degrees), such that the 2D projection images may be used as 2D maps showing the tracking volume from different viewing directions, as discussed below. In certain examples, the projection vectors are orthogonal to planes of the 2D projection images.

In another act of the method, a first reference 2D image is determined by the control unit. A reference 2D image is an image similar to the first and second 2D projection image. It shows the tracking volume under the same viewing direction or projection direction. In particular, a reference 2D image depicts features of the patient in the tracking image, which do not change with the movement of the medical instrument. Such a reference 2D image may be derived from a separate image acquisition in absence of the medical instrument. Alternatively, a reference 2D image may be computed by the control unit from previous first and second 2D images, eliminating the variable effects caused by the moving medical instrument.

In another act of the method, in a similar way, a second reference 2D image is determined by the control unit, having the same viewing direction or projection direction as the second 2D projection image.

In another act of the method, a background is suppressed or removed from the first 2D image as a function of the first reference 2D image by the control unit. As the first 2D reference image and the first 2D image represent the same volume from the same perspective, the background may be suppressed by a subtraction of the pixel values of the first 2D image minus the first 2D reference image. As the images may differ slightly by contrast or an offset, some corrections may be required to achieve best results. The pixel values may be scaled by a linear function y=ax+b before subtracting, wherein y is the pixel value for the first 2D image and x the pixel value for the first 2D reference image. The values for the scaling function may be determined by an optimization problem, e.g., minimizing the sum of the square values of the difference of the image pixel values (LSQR).

In another act of the method, the control unit determines a first set of coordinates of the medical instrument from the first 2D image after background suppression. In this image, major contrast shall be caused by the medical device. For example, an algorithm for detecting areas of high contrast may therefore be applied to determine the contour of the medical instrument. Other image analysis algorithms may be used, as well as neuronal networks and/or AI trained with images of the medical instrument at known coordinates. With the coordinates of the contour in the image, coordinates of the medical instrument in the plane of the image may be determined using the mapping relation of the imaging process of the magnetic resonance tomograph.

In a similar way, in another two acts of the method, a background is suppressed or removed from the second 2D image as a function of the second reference 2D image by the control unit and a second set of coordinates in the image plane of the second 2D reference image or the second 2D image of the medical instrument is determined from the second 2D image by the control unit.

In other words, at least two set of coordinates in two planes at different orientations in space are known, which define a position of the medical instrument, (i.e., at least one point like the tip), in three dimensional space.

In another act of the method, the 3D coordinate is extracted from the two sets of coordinates in the two planes. As the planes have different and known orientation in space, the two coordinate sets in the two planes define a position in 3D space, which is derived by coordinate transformation by the control unit.

In an advantageous manner, the method allows a quick detection and 3D tracking of the medical instrument with the magnetic resonance tomograph.

The magnetic resonance tomograph configured to execute the method shares the benefits of the method as described herein.

In an embodiment of the method, the method further includes outputting the 3D position of the medical instrument to a user. The 3D position may be depicted in a 3D-rendered image, a virtual reality device, or by a plurality of 2D images from different view aspects. It is also conceivable that the 3D position is output in numerical values or coordinates.

The visual display of the coordinates eases in a beneficial way the navigation of the medical instrument by a user.

In an embodiment of the method, the control unit determines the first reference 2D image from a plurality of first 2D projection images and/or determines the second reference 2D image from a plurality of second 2D projection images. As discussed before, the reference 2D images shall depict features in the tracking volume, which do not change with the movement of the medical instrument and may be subtracted as background from the 2D projection images to ease detection of the medical instruments. Such reference 2D images may be derived from a plurality of 2D projection images by selecting or filtering constant image content. In one example, a plurality of 2D projection images may be averaged, such that constant content adds up while changing content is reduced. Median functions may be applied that identify and suppress pixels changing in consequent 2D projections. The determination may also depend on the signal generated by the medical device. For example, a metallic instrument causes extinction of the magnetic resonance (MR) signal in a surrounding volume, while a catheter filled with contrast agent like a Gadolinium solution may cause a strong positive signal.

In a beneficial way, generating the reference 2D images from 2D projection images allow a continuous update of the background signal and saves time for separate acquisition of reference 2D images.

In an embodiment of the method, the method further includes acquiring a 2D slice including the medical instrument by the magnetic resonance tomograph. Within this act, the control unit determines the position of the 2D slice in dependence of the first set of coordinates and/or second set of coordinates. The control unit may determine a 3D coordinate in space as explained before and then determine a plane that includes the 3D coordinates of the medical instrument, which may be provided by the coordinate of the tip of the medical instrument and the direction of extension. The slice to be imaged is the cross section of this plane and the field of view.

In a beneficial way, the acquisition of the slice allows to show the user the medical instrument together with the environment in the body of a patient.

In another embodiment of the method, the control unit determines the first reference 2D image by acquiring a third 2D projection image of the tracking volume in absence of the medical instrument in the tracking volume with the magnetic resonance tomography unit and/or determines the second reference 2D image by acquiring a fourth 2D projection image of the tracking volume in absence of the medical instrument in the tracking volume with the magnetic resonance tomography unit. In other words, the reference 2D images are acquired by the control units with separate image acquisitions of 2D projection images. These reference 2D images are acquired when the medical instrument is not present in the tracking volume, such that no signals caused by the medical instrument are part of the reference 2D images. The reference 2D images may be acquired in advance to the intervention. The acquisition may be performed using a fat suppressing sequence, e.g., a Dixon sequence or a sequence using a fat saturating pre-pulse or a water selective exciting pulse. Also, all other image improving acts explained before may be applied.

In a beneficial way, the acquisition of reference 2D images without presence of the medical instrument eases detection of the medical device in subsequent images.

In an embodiment of the method, the acquiring of a 2D projection image of the tracking volume includes exciting the spins in the tracking volume by an excitation pulse at the same time with the same excitation pulse. This might be caused with a narrow-band excitation pulse at Larmor frequency in a homogeneous B0 magnetic field. It is also conceivable to use a broadband excitation pulse as a magnetic gradient field is applied at the same time. The bandwidth of the pulse is determined by the strength of the gradient and the dimension of the tracking volume along the axis of the gradient. This selection of a single slice limited to the tracking volume suppresses signals from outside the tracking volume at least in direction of the gradient axis.

To provide a 2D projection image during readout only, a 2D encoding scheme, (e.g., phase encoding), is applied in the sequence. By applying only encoding in two dimensions, (e.g., x- and y-axis), there is no differentiation for the MR signals of the volume elements along the third axis and the MR signals of the volume elements are summed up.

In a beneficial way, with a 2D encoding, the complete tracking volume may be acquired in a single acquisition in a 2D projection image.

In another embodiment of the method, the defined tracking volume is divided by the control unit into a stack of slices. For the cuboid described before, such slices may be provided by splitting the cuboid by a plurality of planes parallel to one of the surfaces of the cuboid. The planes may be positioned equidistant, e.g., each slice having a same thickness or dimension along the normal vector of the planes. As the geometry of imaging with the magnetic resonance tomograph is distorted by field inhomogeneities, the slices may also be maps of the ideal planar planes described before, distorted by the magnetic resonance tomographs imperfection. In certain examples, the slices are arranged along an axe of the image acquisition such that the hereinafter described act of projection may be performed as easy as possible.

In another act of the method, the magnet resonance tomograph acquires a first one-dimensional (1D) projection for each slice. The spins to be detected in the slices are excited by an excitation pulse with a magnetic gradient applied in orthogonal direction to the slice. A 1D projection is an image acquisition, wherein an encoding for spatial resolution is only applied in one dimension. In other words, for a two-dimensional slice, (i.e., a slice that has in direction of thickness only a single layer of volume elements to be acquired/imaged), an encoding is provided only along one axis. As a result, the signal generated and acquired for any spot along this axis represents an integral of the signals of all volume elements of the slice along a projection line through the axis at this spot and perpendicular to the axis in the plane of the slice. The value generated for each spot represents the integral of the spins along the projection line, similar to the electron density for of an x-ray image.

In another act of the method, the generated 1D projections for all slices are combined to a 2D projection image by the control unit. Like the lines of a TV image, the lines of the 1D projections are aligned in parallel, thereby providing an image of the stack of slices in a perspective parallel to the slices and perpendicular to the axis.

In another act, a second 1D projection for each slice is acquired by the magnetic resonance tomograph in a second projection direction, wherein the first projection direction and the second projection direction enclose an angle larger than 45 degrees, larger than 60 degrees, larger than 80 degrees, or 90 degrees.

In another act, and in a similar way as described before, the stack of second 1D projections is combined by the control unit to a second 2D projection image. The perspective of the second reference image is turned relative to the first reference image around the axis by the angle, (e.g., by 90 degrees), to provide a view from two different sides of a cube which eases the navigation of the medical instrument by a user.

In a beneficial way, the acquisition of single slices makes it possible to cover also tracking volumes with large dimensions.

In an embodiment of the method, the method further includes acquiring an MR image for a 2D slice including the medical instrument, wherein the control unit determines the position of the 2D slice in dependence of the first set of coordinates and/or second set of coordinates. As the position of the medical instrument has been determined, the control unit calculates a plane with position and orientation, such that the medical instrument lies in the plane/slice. The control unit acquires then a 2D image of the slice with the magnetic resonance unit and may present the image to an operator.

In a beneficial way, the method allows to provide 2D images with the medical instrument updated with a high frequency.

In an embodiment of the method, the determining of the reference 2D images are repeated for different positions of a patient. The position is not limited to the externally visible position of the patient, but particularly includes a position of organs within the tracking volume. The position of organs may change during breathing and/or heartbeat. The different positions may include different phases of heartbeat or breathing. A plurality of first reference 2D images and second reference 2D images are generated by the control unit. As the 2D projection images are acquired at different positions, each of the plurality of the first reference images and of the second reference images represent a different breathing position. In other words, a library of reference images is prepared for a plurality of breathing and/or heartbeat positions, for all breathing positions, and/or for all heartbeat positions.

In a beneficial way, background information is provided for different breathing positions that enables tracking at any time.

In an embodiment of the method, during the removing of the background, the control unit selects the first reference 2D image of the plurality of first reference 2D images, which is most similar to the first 2D projection image. "Most similar" means that the difference between the reference image and a target image with the medical instrument for tracking is the least. For example, the reference image from the plurality of reference 2D images may be chosen, for which a sum of the squares of the difference of the pixel values between reference image and the target images is minimal. "Most similar" may also mean that a correlation function provides the highest value for the two images. There may also be some preprocessing, like displacement of the images, rotation, scaling or adjustment of lightness and/or contrast.

In a beneficial way, the peak detection selection of the reference with the least difference eases detection of the medical instrument.

In an embodiment of the method, a fat suppressing sequence is used in the acquiring of a first 2D projection image and/or the acquiring of a second 2D projection image. Such sequence may be a Dixon sequence or a sequence using a fat saturating pre-pulse or a water selective exciting pulse.

In a 2D projection image acquisition, fat accumulations along the projection path may dominate result of the projection. In a beneficial way, a fat suppression technology may be used to reduce the fat signal and make the medical instrument visible in the projection.

In an embodiment of the method, a peak detection algorithm is applied in the determining of a first set of coordinates of the medical instrument from the first 2D image and/or the determining of a second set of coordinates of the medical instrument from the second 2D image. Such peak detection algorithm may use algorithms for a simple high-pass filter for increasing the contrast of a border, border detection, or even a neuronal network trained with different images of the medical instrument at different positions. Parametrized models of the medical instruments may also be used in an optimization with LSR to determine the position of the medical instrument. In certain examples, the peak detection is applied to a 2D projection image after removing the background.

In a beneficial way, the peak detection algorithms speed up and make the detection of the medical instrument more reliable.

In an embodiment of the method, the medical instrument is a catheter. A catheter may differ in the way it is imaged by the magnetic resonance tomography unit. Instead of extinction of the signal by metal, a contrast agent in the catheter may provide a strong signal. In a beneficial way, the method is independent on the kind of signal.

The tomography unit is configured to perform the method as described herein. The magnetic resonance tomography unit may be configured to perform the method by loading a computer program product from a storage media into a memory of the control unit and executing the program.

The characteristics, features, and advantages described above and also the manner in which these are achieved become clearer and easier to understand in conjunction with the description given below of the embodiments, which are explained in greater detail in conjunction with the drawings.

DETAILED DESCRIPTION

Figure 1:
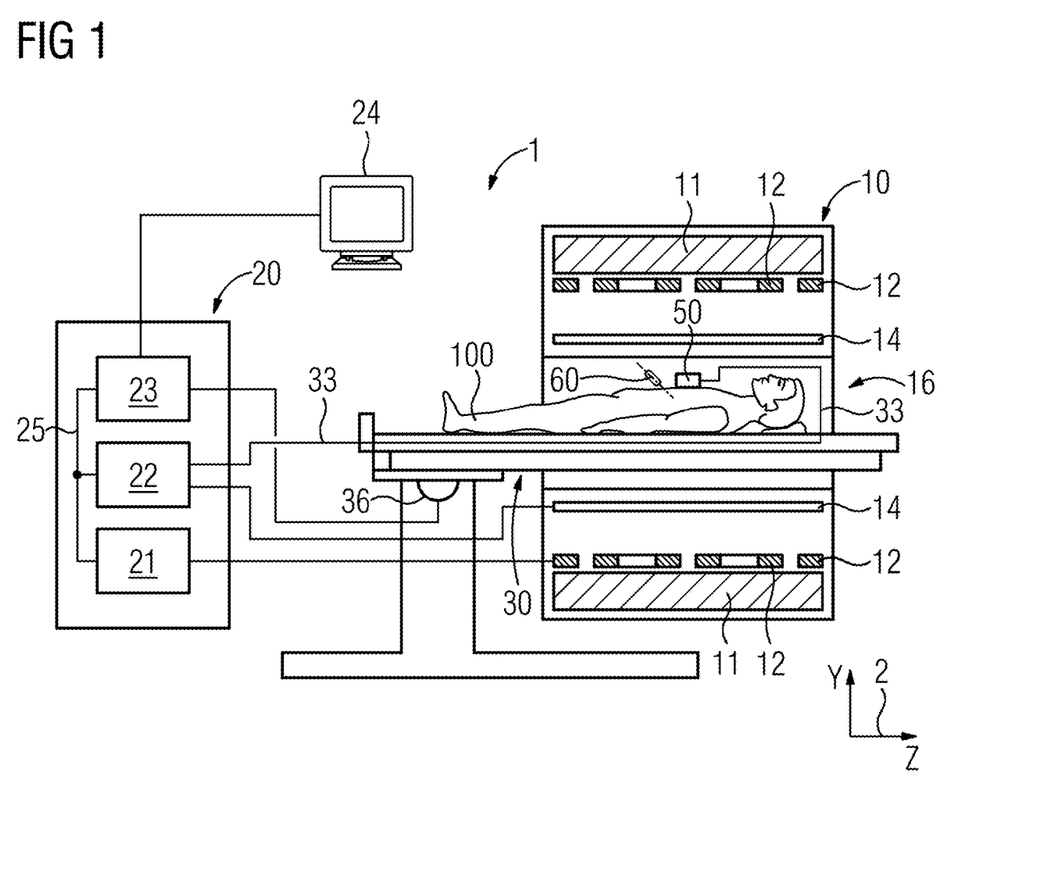
FIG. 1 depicts an example of a schematic diagram of a magnetic resonance tomography unit.

FIG. 1 shows a schematic diagram of a form of embodiment of a magnetic resonance tomography unit 1.

The magnet unit 10 has a field magnet 11, which generates a static magnetic field B0 for alignment of nuclear spins of samples or patients 100 in a recording region. The recording region is arranged in a patient tunnel 16, which extends in a longitudinal direction 2 through the magnet unit 10. A patient 100 may be moved by the patient couch 30 and the drive unit 36 of the patient couch 30 into the recording region. The field magnet 11 may involve a superconducting magnet, which may provide magnetic fields with a magnetic flux density of up to 3T, with the very latest devices of even more. For lower field strengths however permanent magnets or electromagnets with normally conducting coils may be employed.

The magnet unit 10 furthermore has gradient coils 12, which are designed, for spatial differentiation of the recorded imaging regions in the examination volume, to superimpose variable magnetic fields in three spatial directions on the magnetic field B0. The gradient coils 12 may be coils made of normally conducting wires, which may generate fields orthogonal to each other in the examination volume.

The magnet unit 10 likewise has a body coil 14 configured to radiate a radio-frequency signal supplied via a signal line into the examination volume and to receive resonant signals emitted by the patient 100 and output them via a signal line 33. In one example, however, the body coil 14 is replaced, for sending out the radio-frequency signals and/or receiving them, by the local coil 50, which is arranged in the patient tunnel 16 close to the patient 100. It is also conceivable, however, for the local coil 50 to be configured for sending and receiving, and therefore a body coil 14 may be omitted.

A control unit 20 supplies the magnet unit 10 with the various signals for the gradient coils 12 and the body coil 14 and evaluates the received signals. A magnetic resonance tomography unit controller 23 coordinates the subunits in this case.

The control unit 20 has a gradient control 21 configured to supply the gradient coils 12 via supply leads with variable currents, which provide the desired gradient fields coordinated in time in the examination volume.

The control unit 20 furthermore has radio-frequency unit 22 configured to generate a radio-frequency pulse with a predetermined timing curve, amplitude, and spectral power distribution to excite a magnetic resonance of the nuclear spins in the patient 100. In this case, pulse powers in the range of kilowatts may be achieved. The individual units are linked to one another via a signal bus 25.

The radio-frequency signal generated by the radio-frequency unit 22 is conveyed via a signal connection to the body coil 14 and emitted into the body of the patient 100 in order to excite the nuclear spins there. Also conceivable is an emission of the radio-frequency signal via one or more coil windings of the local coil 50.

The local coil 50 then may receive a magnetic resonance signal from the body of the patient 100, wherein, because of the short distance, the signal-to-noise ratio (SNR) of the local coils 50 is better than a receipt by the body coil 14. The MR signal received by the local coil 50 is preprocessed in the local coil 50 and forwarded to the radio-frequency unit 22 of the magnetic resonance tomography unit 1 for evaluation and image acquisition.

The signal connection between local coil 50 and magnetic resonance tomography unit 1 may be via a signal line 33 or wireless.

The medical instrument 60 may be guided by an operator using the imaging capabilities of the magnetic resonance tomography unit 1 with the method as discussed below.

Figure 2:
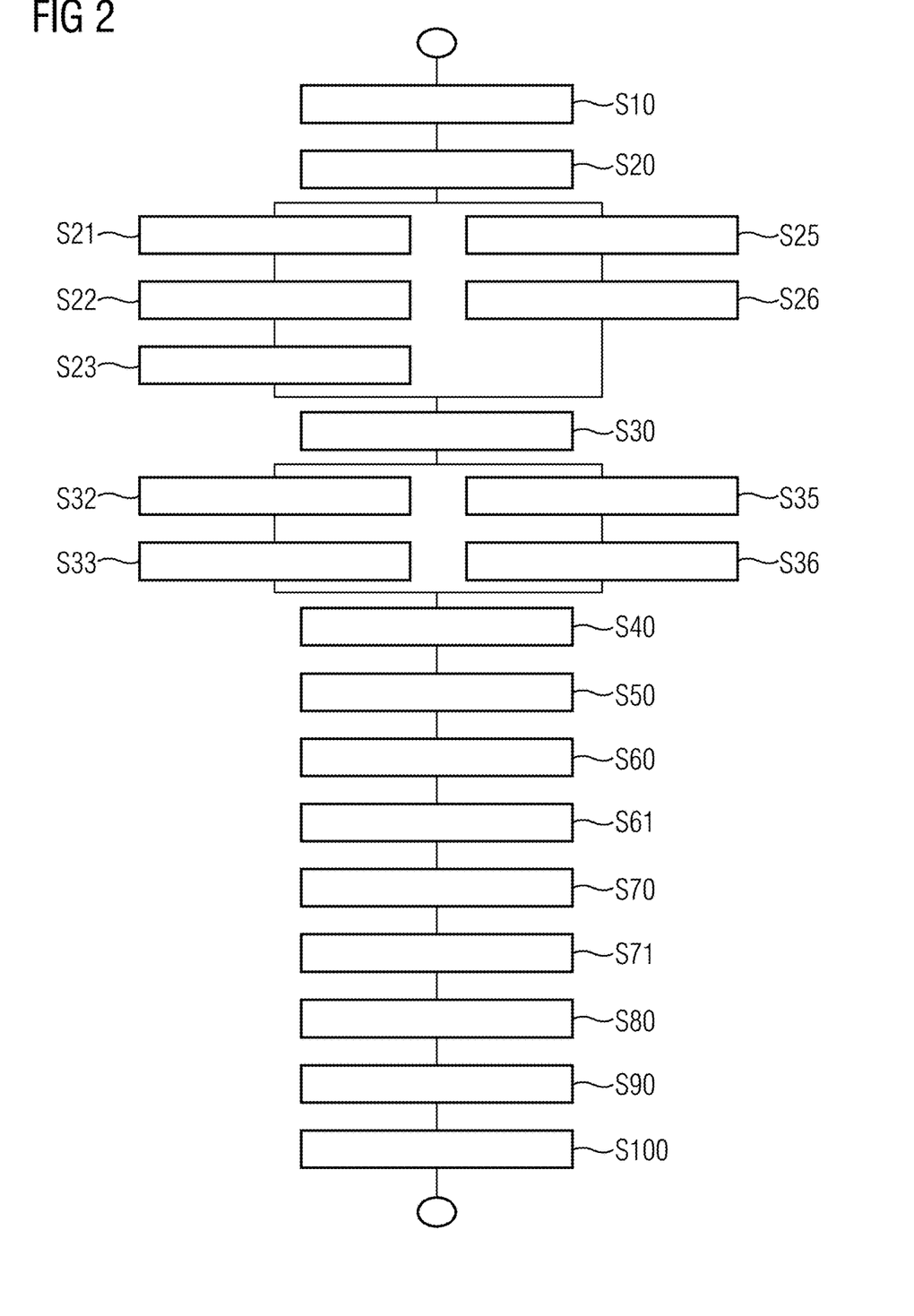
FIG. 2 depicts an example of a flow chart of the method.

FIG. 2 shows a flow chart of an embodiment of the method for tracking a medical instrument.

The method is executed by a magnetic resonance tomography unit including 1 a control unit 20 configured to perform the image acquisition with the magnetic resonance tomography unit 1 and, e.g., the method as described herein.

In act S10, a tracking volume 70 is defined by the control unit 20, which encloses a predefined trajectory 71. The trajectory 71 may be derived from a 3D model of the patient 100 by an operator. The trajectory 71 may be a linear path between an entrance point and a target destination in the body of a patient 100. The trajectory 71 may also be curved, e.g., in case the medical instrument is a catheter, and it is delimited by a vessel of a patient. A tracking volume 70 may be defined by a cuboid with the coordinates of the corners given by the minima and maxima of the x, y, z-coordinates of all points along the trajectory 71.

In act S20, a first 2D projection image of the tracking volume in presence of the medical instrument is acquired by the control unit 20 using the magnetic resonance tomography unit 1. A 2D projection image is an image, which depicts a 3D volume by an 2D image in a plane or piece of a plane by a projection of volume elements along a projection vector or projection direction onto the plane. Two exemplary different ways of acquiring such 2D image projections explained in the following paragraphs.

A 2D projection image may be acquired by first providing 1D projections of multiple slices of a volume and combining then these 1D projections to a 2D projection image.

In act S21, the tracking volume 70 is therefore divided into a stack of slices 72 by the control unit 20. A slice 72 may be a two-dimensional layer of volume elements to be imaged, e.g., arranged in a plane. The plane may be distorted or warped by non-linearities of the gradient system. The stack of slices 72 may be arranged along the longitudinal direction 2 along the z-axis parallel to the B0 magnetic field, wherein the planes of the slices 72 are perpendicular to the z-axis. Any other orientation of the stack is considerable, e.g., along x-axis or y-axis or any linear combination thereof.

In certain examples, the slices 72 of a stack are of equal thickness and/or the planes are arranged at equal distance and fully cover the tracking volume 70 such that there is no place inside the tracking volume 70 that is not included when acquiring MR data for all volume elements 73 of the slices 72.

Figure 3:
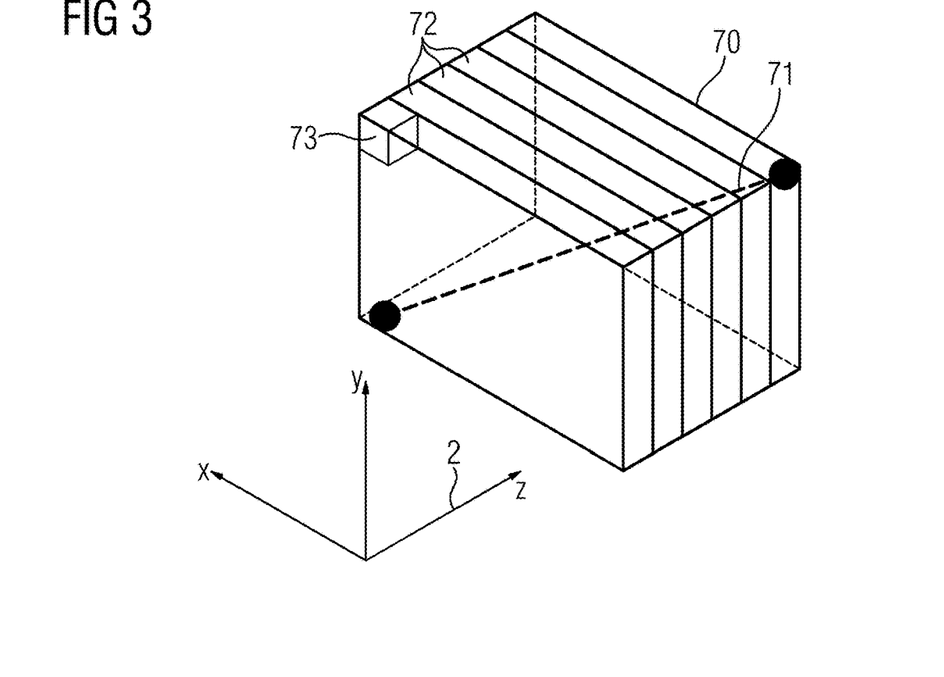
FIG. 3 depicts an example of a schematic view of a tracking volume with a trajectory.

In FIG. 3, such an exemplary stack of slices 72 is shown. For simplicity of the drawing, the slices are arranged in parallel to the x-y-plane of the coordinate system and the stack of slices 72 is arranged along the z-direction. Only a single volume element 73 is shown, but each of the slices is fully covered by a matrix of such volume elements 73.

In act S22, the control unit 20 acquires a first 1D projection for each slice 72, using the magnetic resonance tomography unit 1.

Figure 4:
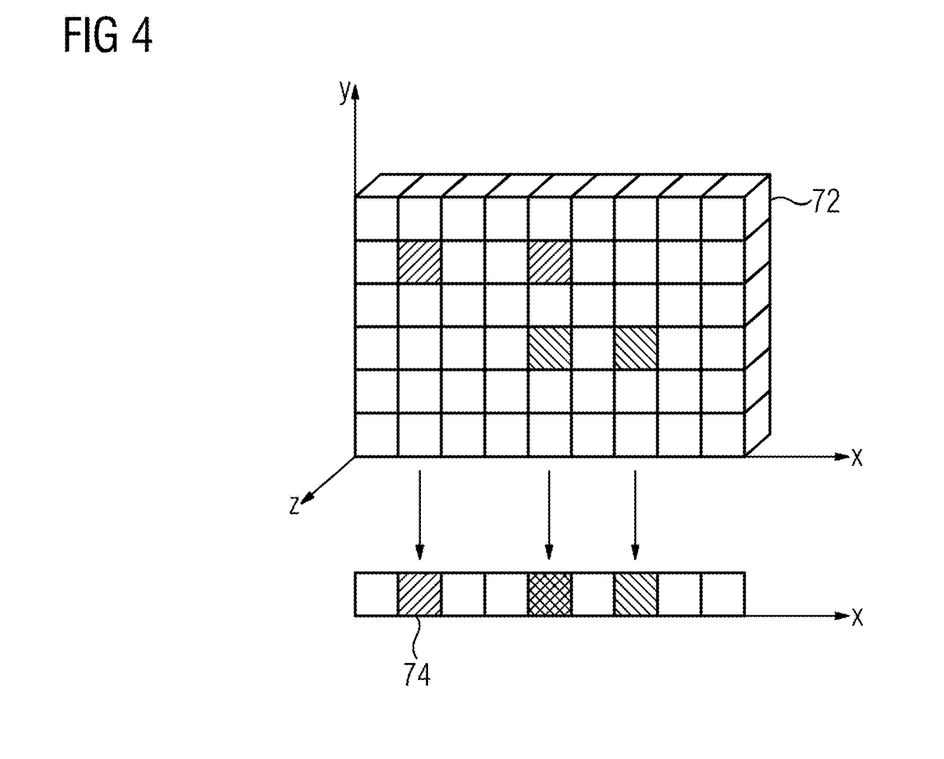
FIG. 4 depicts an example of a schematic view of a 1D projection of a slice.

An example of a 1D-projection is shown in FIG. 4 for a single slice 72. The slice 72 is arranged parallel to the x-y-plane. Such a slice 72 may be captured by sending an excitation pulse for a narrow frequency band while a z-gradient magnetic field is applied by the control unit 20 using the gradient coils. The position along the z-axis is defined by the center frequency of the pulse while thickness of the slice 72 along the z-axis is defined by the bandwidth of the pulse.

In the example of FIG. 4, only a one-dimensional encoding is applied to the slice 72 such that MR signals with the same x-coordinate experience the same phase shift, independently from the y-coordinate. In the readout, all MR signals from a column with same x-coordinate are summed up. Signals deriving from different y-coordinates are summed up and cannot be separated anymore. This is similar to a simple x-ray image, summing up the attenuation factors of all volume elements along the direction of the x-ray beam, here equal to the y-axis. Thereby, each slice 72 is reduced to an image line 74 of pixels, similar to the lines on an old cathode ray tube.

In act S23, the stack of first 1D projections is combined by the control unit 20 to a first 2D reference image. Following the example of FIG. 4, the resulting image lines 74 in are arranged in parallel to each other in the x-z-plane such that the pixel elements of each image line 74 in x-direction together with the neighboring pixels of the other slices 72 complement to a two-dimensional image in the x-z-plane. In a beneficial way, the image provides x-z coordinates for any object in the slices 74 above the x-z-plane independent from the y coordinate in the slices 74 by the projection along the y-axis.

Figure 6:
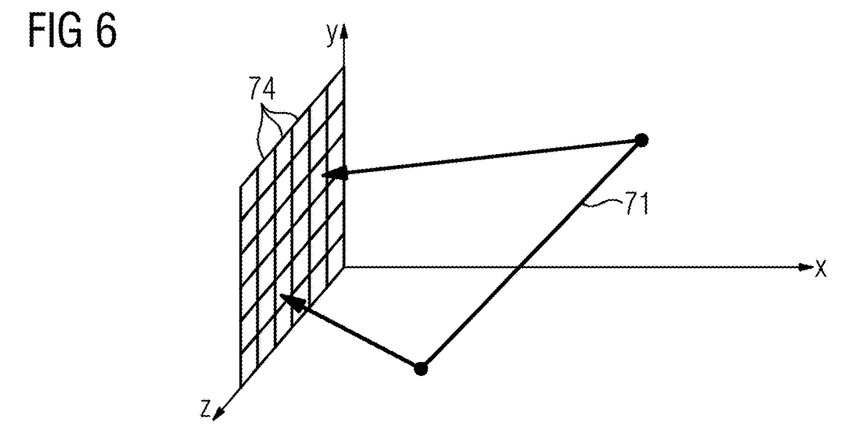
FIG. 6 depicts an example of a schematic view of a projection of the trajectory onto a y-z-plane.

In acts S32 and S33, the acts S22 and S23 are repeated with another coordinate system, e.g., the roles of x and y axis may be swapped such that the slices are projected along the x-axis onto an image line 74 extending along the y-axis, as shown in FIG. 6. This is equivalent to a rotation of the coordinate system around the z-axis by 90 degrees. The idea behind is that the projections in two different directions each provide a pair of two coordinates for each point projected. If the projection directions are not parallel and may include an angle larger than 45 degrees, larger than 60 degrees, or equal to 90 degrees, the two pairs of two-dimensional coordinates in the projections may be used to determine a three-dimensional coordinate of each point projected.

Figure 7:
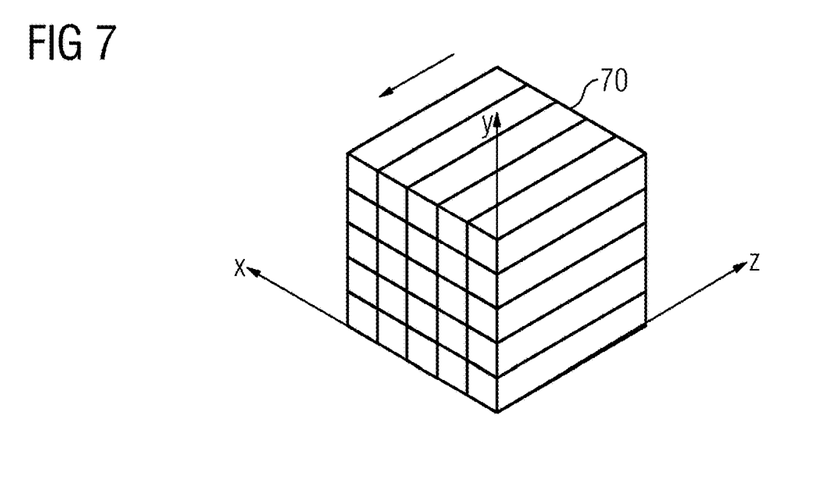
FIG. 7 depicts an example of a schematic view of a 2D image projection using 2D encoding.

Alternatively, a 2D projection image may also be acquired with 2D encoding. As shown in FIG. 7, the tracking volume 70 may also be seen as a single slice, which is subdivided in columns in the x-y-axis extending in z-direction through the slice. In a similar way, a single slice may be defined in the y-z-plane with columns extending in x-direction.

For the 2D encoding, all spins to be imaged in the slice have to be excited first by an excitation pulse. This may be achieved in acts S25 and S35 by a narrowband pulse at the Larmor frequency in absence of magnetic gradient field. But in this case, also spins outside the tracking volume 70 may be excited and contributed to the MR signal. Alternatively, the excitation may be limited to the thickness of the single slice by applying a broadband excitation pulse, wherein the bandwidth is determined by the applied magnetic gradient in direction of the thickness of the slice and the thickness.

The 2D projection is then acquired by reading out the MR signals for the tracking volume by applying a 2D encoding in acts S26 and S36. The encoding scheme may be a 2D phase encoding.

A second 2D projection image is acquired in acts S35 and S36, wherein at least act 36 differs from act S26 by the plane in which the 2D-encoding is provided. The resulting two 2D projection images show the tracking volume from two aspect directions that enclose an angle larger than 30 degrees, larger than 60 degrees, or equal to 90 degrees.

Figure 5:
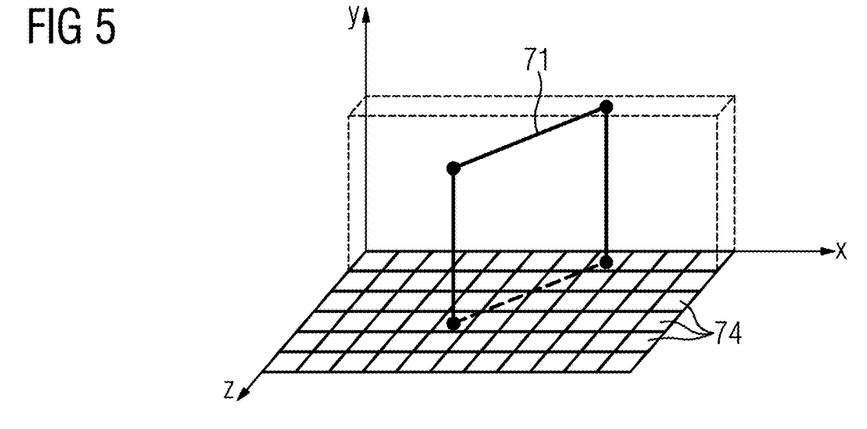
FIG. 5 depicts an example of a schematic view of a projection of the trajectory onto a x-z-plane.

In the examples of FIGS. 5 and 6, the 2D projection images of FIG. 5 provides x-z-coordinates and FIG. 6 y-z-coordinates such that for an object, which may be identified unambiguously in both projections, the coordinates x, y, and z are directly given. For planes at other angles to each other and other orientation to the coordinate system of x, y, and z, a coordinate transformation by a matrix may be necessary.

In act S40, a first reference 2D image is determined by the control unit 20. There are different options how the control unit 20 may perform this act.

A separate 2D projection image may be acquired as explained before in regard to acts S20 and S30, but in absence of the medical instrument, such that the reference 2D image only depicts the patient 100.

It is also conceivable, that the control unit 20 provides a library of reference 2D images by acquiring a series of 2D projection images at different positions of the patient 100. The position is not limited to the body surface of the patient 100 but is in particular related to the organs of the patient 100 in the tracking volume, which may change their position, e.g. as the patient breaths or with the heartbeat. The library or atlas of 2D reference images may cover different phases of the heartbeat and/or breathing cycle.

It is also conceivable that the control unit 20 makes use of already acquired 2D projection images for determining a background image. As the position of the medical instrument 60 changes during tracking the instrument, the control unit may filter out constant parts of the 2D projection images to retrieve a background. This may be achieved by averaging a plurality of images or applying a median function. Also, a filter may be applied which reflects the way how the medical instrument is imaged by the magnetic resonance tomography unit 1, e.g., signal extinction.

In a similar way, in act S50, the control unit 20 determines a second reference 2D image or a library of reference 2D images. The difference is the projection direction or view angle. While the first reference 2D image in act S40 depicts the tracking volume 70 at the same view angle and provides a 2D projection image at the same projection direction than the first 2D projection image, the second 2D reference image depicts the tracking volume 70 at the same view angle than the second 2D reference image.

In act S60, the control unit 70 suppresses the background from the first 2D projection image as a function of the first reference 2D image. The control unit 70 may subtract the pixel values of the reference 2D image from the 2D projection image. The reference 2D image may be scaled or distorted before to adjust variations in the image acquisition. The preprocessing may be parametrized and the parameters may be optimized for minimum energy of the resulting differential image.

When a library or atlas of reference 2D images has been acquired for different positions of the patient, the control unit may first select a reference 2D image for background removal from the library which is next to the first 2D projection image. Next may be measured by a metric that may be provided by a correlation function between 2D projection image and reference 2D image or a minimum energy of a difference image.

The removal of the background, which may include the organs of the patient 100 in the tracking volume, simplifies the next act.

In act S61, a first set of coordinates of the medical instrument from the first 2D image by the control unit.

After the removal of the background, the remaining 2D differential image basically shows the medical instrument 60 or artefacts caused by the medical instrument. A pixel belonging to the medical instrument 60 may be e.g. detected by the fact that the pixel value differs from the average image offset.

The coordinates of the pixels in the image matrix with the signal from the medical instrument 60 define thereby also two coordinates of the medical instrument 60 in the tracking volume. The 2D differential image may also be preprocessed by a filter, e.g., a high pass filter to increase the contrast of the edges of the medical instrument. Also a parametrized model for the medical instrument 60 may be fitted to the 2D differential image to determine the coordinates in act S61.

In a similar way, in act S70, the control unit 20 suppresses the background from the second 2D projection image using the second reference 2D image and, in act S71, determines a second set of coordinates from a second 2D differential image retrieved from the second 2D projection image and the second reference 2D image.

In act S80, a set of 3D coordinates is determined from the two sets of 2D coordinates. For an orthogonal coordinate system and the planes of the first 2D projection image arranged, e.g., in the x-y-plane and y-z-plane, the values of the x-y-z coordinates may be derived directly from the coordinates in the planes. For other coordinates, a coordinate transformation may be necessary or solving a linear equation system. It is also conceivable that the coordinates of a plurality of points of the medical instrument 60 are determined in the same way.

The determined 3D position is output in act S90 by the control unit 70 to an operator. The position may be depicted on a display in different 2D projections under different view angles. A 3D image may be rendered using the 3D position or a virtual reality showing the medical instrument 60 and the organs in the tracking volume. It is also conceivable to output the 3D coordinates numerically.

In act S100, the control unit 20 may determine a position of a slice which includes the medical instrument 70, acquire an MR image of the slice, and show the image on a display to the operator.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A magnetic resonance tomography unit for tracking a medical instrument, the magnetic resonance tomography unit comprising:
a controller configured to:
define a tracking volume enclosing a predefined trajectory;
acquire a first two-dimensional (2D) projection image of the tracking volume in presence of the medical instrument with the magnetic resonance tomography unit;
acquire a second 2D projection image of the tracking volume in presence of the medical instrument with the magnetic resonance tomography unit, wherein a first projection vector of the first 2D projection image and a second projection vector of the second 2D projection enclose an angle larger than 20 degrees;
determine a first reference 2D image;
determine a second reference 2D image;
suppress a background from the first 2D projection image as a function of the first reference 2D image to provide a background suppressed first 2D image;
determine a first set of coordinates of the medical instrument from the background suppressed first 2D image;
suppress a background from the second 2D projection image as a function of the second reference 2D image to provide a background suppressed second 2D image;
determine a second set of coordinates of the medical instrument from the background suppressed second 2D image; and
determine a three-dimensional (3D) position of the medical instrument from the first set of coordinates and the second set of coordinates.

2. The magnetic resonance tomography unit of claim 1, wherein the controller is further configured to output the 3D position of the medical instrument to a user.

3. The magnetic resonance tomography unit of claim 1, wherein the first reference 2D image is determined from a plurality of first 2D projection images, and/or
wherein the second reference 2D image is determined from a plurality of second 2D projection images.

4. The magnetic resonance tomography unit of claim 1, wherein the first reference 2D image is determined by acquiring a third 2D projection image of the tracking volume in absence of the medical instrument in the tracking volume with the magnetic resonance tomography unit, and/or
wherein the second reference 2D image is determined by acquiring a fourth 2D projection image of the tracking volume in absence of the medical instrument in the tracking volume with the magnetic resonance tomography unit.

5. The magnetic resonance tomography unit of claim 1, wherein the controller is further configured to acquire a 2D projection image of the tracking volume by transmitting an excitation pulse for exciting spins in the tracking volume and acquiring a 2D image by reading out magnetic resonance (MR) signals from the tracking volume with a 2D encoding.

6. The magnetic resonance tomography unit of claim 1, wherein the controller is further configured to acquire a 2D projection image of the tracking volume by:
dividing the tracking volume into a stack of slices;
acquiring a first one-dimensional (1D) projection for each slice in a first projection direction with the magnetic resonance tomography unit;
combining a stack of first 1D projections to the first 2D projection image;
acquiring a second 1D projection for each slice in a second projection direction with the magnetic resonance tomography unit, wherein the first projection direction and the second projection direction enclose an angle larger than 45 degrees; and
combining a stack of second 1D projections to the second 2D projection image.

7. The magnetic resonance tomography unit of claim 1, wherein the controller is further configured to:
acquire a magnetic resonance (MR) image for a 2D slice comprising the medical instrument; and
determine the position of the 2D slice in dependence of the first set of coordinates and/or second set of coordinates.

8. The magnetic resonance tomography unit of claim 1, wherein the controller is further configured to provide a plurality of first reference 2D images and/or a plurality of second reference 2D images by repeating the determination of a first reference 2D image and/or the determination of a second reference 2D image at different positions of a patient, and
wherein each first reference 2D image of the plurality of the first reference 2D images and/or each second reference 2D image of the plurality of second reference 2D images represents a different position of the patient.

9. The magnetic resonance tomography unit of claim 8, wherein the controller is further configured to:
select for removing the background the first reference 2D image of the plurality of first reference 2D images that is most similar to the first 2D image; and/or
select for removing the background from the second reference 2D image of the plurality of second reference 2D images that is most similar to the second 2D image.

10. The magnetic resonance tomography unit of claim 1, wherein the controller is further configured to select a fat suppressing sequence for acquiring a 2D projection image.

11. The magnetic resonance tomography unit of claim 1, wherein the controller is configured to:
determine the first set of coordinates of the medical instrument from the background suppressed first 2D image using a peak detection algorithm; and/or
determine the second set of coordinates of the medical instrument from the background suppressed second 2D image using the peak detection algorithm.

12. A method for tracking a medical instrument with a magnetic resonance tomography unit comprising a controller, the method comprising:
defining, by the controller, a tracking volume enclosing a predefined trajectory;
acquiring a first two-dimensional (2D) projection image of the tracking volume in a presence of the medical instrument with the magnetic resonance tomography unit;
acquiring a second 2D projection image of the tracking volume in presence of the medical instrument with the magnetic resonance tomography unit, wherein a first projection vector of the first 2D projection image and a second projection vector of the second 2D projection enclose an angle larger than 20 degrees;
determining, by the controller, a first reference 2D image;
determining, by the controller, a second reference 2D image;
suppressing, by the controller, a background from the first 2D projection image as a function of the first reference 2D image to provide a background suppressed first 2D image;
determining, by the controller, a first set of coordinates of the medical instrument from the background suppressed first 2D image;
suppressing, by the controller, a background from the second 2D projection image as a function of the second reference 2D image to provide a background suppressed second 2D image;
determining, by the controller, a second set of coordinates of the medical instrument from the background suppressed second 2D image; and determining, by the controller, a three-dimensional (3D) position of the medical instrument from the first set of coordinates and the second set of coordinates.

13. The method of claim 12, wherein the determining of the first 2D reference image and the determining of the second 2D reference image are repeated at different positions of a patient to provide a plurality of first reference 2D images and a plurality of second reference 2D images that represent different positions of the patient, and wherein during the suppressing of the background from the first 2D projection image, the controller selects a first reference 2D image of the plurality of first reference 2D images that is most similar to the first 2D image, and/or wherein during the suppressing of the background from the second 2D projection image, the controller selects a second reference 2D image of the plurality of second reference 2D images that is most similar to the second 2D image.

14. The method of claim 12, wherein the medical instrument is a catheter.

15. A computer program product comprising a computer program configured to be directly loaded into a controller of a magnetic resonance tomography unit, wherein the computer program, when executed by the controller, is configured to cause the controller to:

define a tracking volume enclosing a predefined trajectory;
acquire a first two-dimensional (2D) projection image of the tracking volume in a presence of a medical instrument;
acquire a second 2D projection image of the tracking volume in the presence of the medical instrument, wherein a first projection vector of the first 2D projection image and a second projection vector of the second 2D projection enclose an angle larger than 20 degrees;
determine a first reference 2D image;
determine a second reference 2D image;
suppress a background from the first 2D projection image as a function of the first reference 2D image to provide a background suppressed first 2D image;
determine a first set of coordinates of the medical instrument from the background suppressed first 2D image;
suppress a background from the second 2D projection image as a function of the second reference 2D image to provide a background suppressed second 2D image;
determine a second set of coordinates of the medical instrument from the background suppressed second 2D image; and
determine a three-dimensional (3D) position of the medical instrument from the first set of coordinates and the second set of coordinates.

* * * * *